United States Patent
Shi et al.

(10) Patent No.: US 10,005,744 B2
(45) Date of Patent: Jun. 26, 2018

(54) COMPOUNDS FOR THE TREATMENT OR PREVENTION OF BREAST CANCER

(71) Applicant: JIANGSU ATOM BIOSCIENCE AND PHARMACEUTICAL CO., LTD., Jiangsu (CN)

(72) Inventors: Dongfang Shi, Jiangsu (CN); Changjin Fu, Jiangsu (CN); Xi Cheng, Jiangsu (CN); Jianghua Zhu, Jiangsu (CN)

(73) Assignee: JIANGSU ATOM BIOSCIENCE AND PHARMACEUTICAL CO., LTD., Zhejiang (CN)

( * ) Notice: Subject to any disclaimer, the term of this patent is extended or adjusted under 35 U.S.C. 154(b) by 0 days. days.

(21) Appl. No.: 15/572,760

(22) PCT Filed: May 6, 2016

(86) PCT No.: PCT/CN2016/081241
§ 371 (c)(1),
(2) Date: Nov. 8, 2017

(87) PCT Pub. No.: WO2016/180274
PCT Pub. Date: Nov. 17, 2016

(65) Prior Publication Data
US 2018/0134673 A1    May 17, 2018

(30) Foreign Application Priority Data

May 9, 2015 (CN) .......................... 2015 1 0239715

(51) Int. Cl.
*A61K 31/41* (2006.01)
*C07D 293/12* (2006.01)
*A61P 35/00* (2006.01)

(52) U.S. Cl.
CPC ............ *C07D 293/12* (2013.01); *A61K 31/41* (2013.01); *A61P 35/00* (2018.01)

(58) Field of Classification Search
None
See application file for complete search history.

(56) References Cited

U.S. PATENT DOCUMENTS 5,861,424 A * 1/1999 Chen .................... A61K 31/428
514/314

* cited by examiner

*Primary Examiner* — Samantha L Shterengarts
(74) *Attorney, Agent, or Firm* — CBM Patent Consulting, LLC

(57) ABSTRACT

It discloses compounds for the treatment and prevention of breast cancer, which are specifically 2-phenyl benzoselenazole compounds, pharmaceutically acceptable salts thereof and prodrugs thereof. The present invention further discloses pharmaceutical compositions containing the compounds and applications of the compounds in preparing medicines for the treatment and prevention of breast cancer in mammals. The compounds of the present invention can effectively inhibit or reduce the growth or proliferation of breast cancer cells in mammals, with no inhibition effect on the growth of part of the tested cell lines except for the breast cancer cell lines, and are highly selective.

8 Claims, No Drawings

COMPOUNDS FOR THE TREATMENT OR PREVENTION OF BREAST CANCER

This application is the U.S. national phase of International Application No. PCT/CN2016/081241 filed on 6 May 2016 which designated the U.S. and claims priority to Chinese Application Nos. CN201510239715.7 filed on 9 May 2015, the entire contents of each of which are hereby incorporated by reference.

COMPOUNDS FOR THE TREATMENT OR PREVENTION OF BREAST CANCER

Technical Field of the Invention

The present invention belongs to the field of pharmaceutical chemistry. The present invention particularly relates to 2-phenyl benzoselenazole compounds, methods for preparing the compounds, pharmaceutically acceptable salts thereof, prodrugs thereof or pharmaceutical compositions containing the compounds, as applications in preparing medicines for treating or preventing breast cancer of mammals.

Background of the Invention

As common diseases among women, breast diseases mainly include cyclomastopathy, breast fibroadenoma (benign tumor), and breast cancer (MengQingchun, TianYunxia et al., Survey and Analysis of Women Breast Diseases in Shijiazhuang, Hebei Medical Journal, 2012, 34(6):917-919). Female breast cancer has become the world's second most common malignant tumor, a serious threat to women's health. In 2012, there were 1.67 million new women breast cancer cases worldwide, which accounted for 25.2% of all malignancies in females; there were 520,000 breast cancer deaths, which accounted for about 14.7% of all malignant deaths in females. (Bernard W., Stewart, Christopher P., Wild World Cancer Report 2014, The international agency for research on cancer, World Health Organization.)The incidences of breast cancer have obvious geographical distribution differences. Europe and the United States have the highest incidences of breast cancer in the world, and the incidences are relatively low in Asia and Africa(Perera N. M., and Gui G. P., Multi-ethnic differences in breast cancer: current concepts and future directions, Int. J. Cancer, 2003, 106:463-467). Although the rates of breast cancer in Europe and the United States continue to rise, the mortality rates have decreased year by year. This is mainly due to early detection and treatment of the breast cancer patients. However, in Asia and Africa, due to poor detection techniques and treatment means, the morbidity and mortality of the breast cancer are on the rise (Kawamura T., and Sobue T., Comparison of breast cancer mortality in five countries: France, Italy, Japan, the UK and the USA from the WHO mortality database (1960-2000), Jpn. J. Clin. Oncol., 2005, 35(12):758-759). With the changes in the lifestyle, dietary habits, and environmental factors of Chinese females, the breast cancer becomes one of main factors threatening the health of Chinese females.

Clinically, based on the immunohistochemical techniques and according to the level of receptors (ER, PR and HER2) and the cell proliferation genetic markers (Ki-67), there are different subtypes of breast cancer: 1. triple-negative breast cancer (ER, PR and HER2 are all negative); 2.Luminal breast cancer (ER and PR are positive, but HER2 and Ki67 are different in expression); and3. HER2-overexpression in breast cancer (ER and PR deficiency, and HER-overexpression), wherein the triple-negative breast cancer accounts for about 10% to 20% of the breast cancer, which is highest in degree of malignancy and very easy to cause epithelial-mesenchymal transition, and has worse prognosis than other subtypes of breast cancer. Both endocrinotherapy and targeted therapies are ineffective for the triple-negative breast cancer (Tan A. R., and Swain S. M., Therapeutic strategies for triple-negative breast cancer, Cancer J., 2008, 14(6): 43-351).

At present, the breast cancer treatment includes operative treatment, radiation therapy and adjuvant chemotherapy. The operative treatment is still main means for treating early-stage breast cancer. The radiation therapy for the breast cancer is one of important measures for controlling local recurrence after the surgery, and the radiation therapy following the conservative surgery can significantly decrease the local recurrence rate by 75% averagely (Lim M., Belton J. R., Gelman R., et al, A prospective study of conservative surgery without radiation therapy in select patients with stage I breast cancer, Int. J. Radiat., Oncol. Biol. Phys., 2006, 65(4):1149).

The chemotherapy, as a systematic adjuvant treatment method, has attracted extensive attention in the system therapy for the breast cancer. At the very beginning, CMF (cyclophosphamide/methotrexate/fluorouracil), CAF (cyclophosphamide/adriamycin/fluorouracil), FEC and the like are used clinically (Bonadonna G., Brusamolino E., et al, Combination chemotherapy as an adjuvant treatment in operable breast cancer, N. Engl. J. Med., 1976, 294(8):405-410). The emergence of taxanes, such as paclitaxel (Taxol), has greatly improved the survival rate of early breast cancer patients, and has provided help for the treatment of metastatic breast cancer. The mechanism of taxol is that it acts on microtubule system, promotes tubulin polymerization, inhibits depolymerization, and cell cycle migration is blocked in M phase. But the selectivity of taxanes is poor, and there are serious side effects of bone marrow suppression, neurotoxicity, cardiovascular and liver toxicity, allergic reactions, which bring great physical and mental pain to patients. Currently, endocrine therapy has been used as a standard adjuvant therapy for Luminal subtype breast cancer (estrogen receptor/progesterone receptor positive), which can reduce the annual mortality rate of this subtype of breast cancer by more than 31%(Gralow J. R., Burtein H. J., Wood W., Preoperative therapy in invasive breast cancer: pathologic assessment and systemic therapy issues in operable disease, J. Clin. Oncol., 2008, 26(5): 814-819).

Molecular targeted therapy is a hot spot in the field of breast cancer treatment, and many clinical trials have achieved good results in china. Among them, Hessaitin and Lapatinib are highly specific monoclonal antibodies for advanced breast cancer patients with HER2 overexpression; bevacizumab is also effective for taxane resistant advanced breast cancer(Miller K. D., Chap L. I., Holmes F. A., et al, Randomized phase III trial of capecitabine compared with bevacizumab plus capecitabine in patients with previously treated metastatic breast cancer, J. Clin. Oncol., 2005, 23(4): 792-799). However, for patients with triple-negative and HER2-overexpression breast cancer, because of its estrogen receptor and progesterone receptor were negative, so to tamoxifen, letrozole, anastrozole, exemestane and other traditional endocrine therapy had no reaction. Therefore, it is urgent to develop targeted anti breast cancer agents according to different subtypes of breast cancer.

Compounds containing benzothiazole have extensive biological activities (Weekes A. A., and Westwell A. D., 2-Arylbenzothiazole as a privileged scaffold in drug discovery, Curr. Med. Chem., 2009, 16(19):2430-2440). Stevens et al. (W00114354A1) had reported 2-phenyl benzoxazole compounds or 2-phenyl benzothiazoles and their derivatives thereof, which have a highly selective inhibitory activity against breast cancer cells.

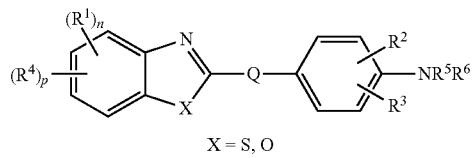

X = S, O

Shi and Aiellohad reported a group of compounds with highly selective inhibitory against breast cancer cell lines (Shi D.-F., Bradshaw T. D., Wrigley S., et al, Antitumour-benzothiazoles. 3. Synthesis of 2-(4-aminophenyl)-benzothiazoles and evaluation of their activities against breast cancer cell lines in vitro and in vivo. [J]. J Med Chem. 1996, 39:3375-3384; Aiello S., Wells G., Stone E. L., et al, Synthesis and biological properties of benzothiazole, benzoxazole, and chromen-4-one analogues of the potent anti-tumor 2-(3,4-dimethoxyphenyl)-5-fluorobenzothiazole (PMX-610, NSC721648), J. Med. Chem., 2008, 51:5135-5139.). The mechanism of action is to induce the expression of CYP1A1 in the P450 enzyme system in the cell, and then metabolized by CYP1A1 to become a highly active substance, inducing tumor cell DNA damage and apoptosis (Bradshaw T. D., Stevens M. F. G., Westwell A. D., The discovery of the potent and selective antitumour agent 2-(4-amino- 3-methylphenyl)benzothiazole(DF203) and related compounds. Curr. Med. Chem., 2001, 8(2):203-210; Rodriguez M. And Potter D. A., CYP1A1 regulates breast cancer proliferation and survival, Mol. Cancer Res. 2013, 11(7):780-792; Wang K. and Guengerich F. P., Bioactivation of fluorinated 2-aryl-benzothiazole antitumor molecules by human cytochrome P450s 1A1 and 2W1 and deactivation by cytochrome P4502S1, Chem. Res. Toxicol., 2012, 25,1740-1751.). Phortress from this group of compounds had entered into phase I clinical study, but the toxicity of the compound to the liver and lungs, and the inability to determine the optimal dose of the treatment terminated the clinical trial. This may be due to the toxicity and defect of the compound itself, and this kind of compound has not been studied further. Currently, Phortress has not been further investigated as an anti-breast cancer drug in clinical use.

Akama et al had reported a series of 5,4'-diamino-6,8,3'-trifluoroflavone compounds, which have good anti-tumor activity, especially for breast cancer cell proliferation inhibition(Akama T., Ishida H., Kimura U., et al, Structure-actuvity relationships of the 7-substituents of 5,4'-diamino-6,8,3'-trifluoroflavone, a potent antitumor agent, J. Med. Chem. 1998, 41, (12):2056-2067).

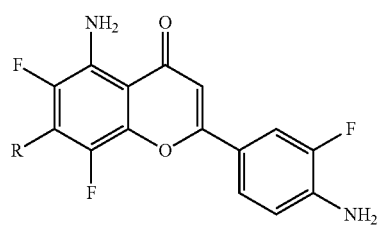

Due to their applications in antitumor, antiviral therapy and nervous system related disease, selenium containing medicines have become a hotspot of the research and development of scholars both in China and foreign countries. The research has mainly focused on anti-tumor, anti-inflammatory, anti-hypertension and the like (Romualdo C., Stefania C., Marina D. G., et al, Novel selenium-containing non-natural diamino acids, Tetrahedron Lett., 2007, 48(7): 1425-1427.). Among them, the role of organic selenium compounds in tumor prevention and treatment has long been widely studied. A large number of studies have shown that organic selenium compounds have definite effect on the resistance of a series of tumors, including colorectal cancer, tumors of digestive tract, respiratory tract cancer, skin cancer, lung cancer, colon cancer, prostate cancer, gastric cancer, liver cancer, breast cancer, ovarian cancer, etc.(El-bayoumy K., and Sinha R., Mechanisms of mammary cancer chemoprevention by organoselenium compounds, Mutat. Res., 2004(551): 181-197.).

SUMMARY OF THE INVENTION

An objective of the present invention is to provide novel 2-phenyl benzoselenazole compounds on the basis of the prior art. The compounds have excellent inhibitioneffect on the growth of breast cancer cell lines, but no inhibitory effect on the growth of some cell lines except breast cancer cell lines. These compounds have good selectivity. This series of compounds may become a new generation of drugs with high selectivity and low toxicity for the treatment of breast cancer.

The objective of the present invention can be achieved by the following schemes.

Compounds of the general formula (I), pharmaceutically acceptable salts thereof or prodrugs thereof are provided:

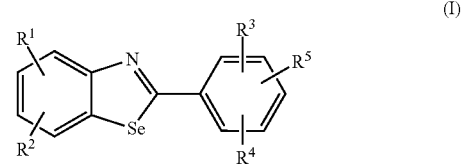

wherein:

$R^1$ and $R^2$ are independently selected from H, D, halogen, —CN, $C_{1-3}$ alkyl, substituted $C_{1-3}$ alkyl, $C_{1-3}$alkoxy or substituted $C_{1-3}$alkoxy, and the substituent group is selected from D, halogen or $C_{1-3}$alkoxy;

$R^3$ and $R^4$ are independently selected from H, D, halogen, —OH, —CN, —$NH_2$, substituted —$NH_2$, $C_{1-3}$ alkyl, substituted $C_{1-3}$ alkyl, $C_{1-3}$alkoxy or substituted $C_{1-3}$alkoxy, and the substituent group is selected from D, halogen, $C_{1-3}$ alkyl or $C_{1-3}$alkoxy; and $R^5$ is selected from H, —OH, —$NH_2$, $C_{1-3}$ alkyl, substituted $C_{1-3}$ alkyl, $C_{1-3}$alkoxy or substituted $C_{1-3}$alkoxy, and the substituent group is selected from D, halogen, —OH, —$NH_2$ or $C_{1-3}$alkoxy.

In a preferred scheme:

$R^1$ and $R^2$ are independently selected from H, D, halogen, —CN, $C_{1-3}$ alkyl, substituted $C_{1-3}$ alkyl, $C_{1-3}$alkoxy or substituted $C_{1-3}$alkoxy, and the substituent group is selected from D, F or $C_{1-3}$alkoxy;

$R^3$ and $R^4$ are independently selected from H, D, halogen, —OH, —CN, —$NH_2$, substituted —$NH_2$, $C_{1-3}$ alkyl, substituted $C_{1-3}$ alkyl, $C_{1-3}$alkoxy or substituted $C_{1-3}$alkoxy, and the substituent group is selected from D, F, $C_{1-3}$ alkyl or $C_{1-3}$alkoxy; and $R^5$ is selected from H, —OH, $NH_2$, $C_{1-3}$alkoxy or substituted $C_{1-3}$alkoxy, and the substituent group is selected from D, F, —OH, —$NH_2$ or $C_{1-3}$alkoxy.

In a preferred scheme, $R^1$ and $R^2$ are independently selected from H, D, F, Cl, —CN, —$CH_3$, —$CF_3$, —$OCH_3$, —$OCH_2CH_3$, —$OCF_3$ or —$OCHF_2$.

In a preferred scheme, $R^1$ and $R^2$ are independently selected from H, D, F, Cl, —CN, —$CH_3$, —$CF_3$, —$OCH_3$ or —$OCH_2CH_3$.

In a preferred scheme, $R^3$ and $R^4$ are independently selected from H, D, halogen, —OH, —CN, —$NH_2$, —$CH_3$, —$CH_2CH_3$, —$CF_3$, —$OCH_3$, —$OCH_2CH_3$, —$OCHF_2$ or —$OCF_3$.

In a preferred scheme, $R^5$ is selected from H, —$NH_2$, —$CH_3$, —$CF_3$, —$OCH_3$, —$OCHF_2$, —$OCF_3$, —$OCH_2CH_3$ or —$OCH_2CF_3$.

As a preferred scheme of the present invention, the compounds of formula (II), pharmaceutically acceptable salts thereof or prodrugs thereof are used:

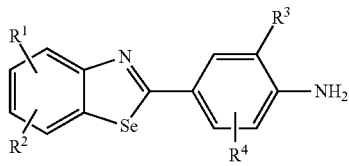

(II)

where $R^1$ to $R^4$ are as defined above.

In a preferred scheme, in the formula (II) or (I), $R^1$ and $R^2$ are independently selected from H, D, F, Cl, —CN, —$CH_3$, —$CF_3$ or —$CHF_2$; and $R^3$ and $R^4$ are independently selected from H, D, F, Cl, Br, I, —CN, —$CH_3$, —$CF_3$, —$OCH_3$, —$OCH_2CH_3$, —$OCHF_2$ or —$OCF_3$.

The present invention further provides the following specific compounds, including pharmaceutically acceptable salts thereof or prodrugs thereof:

4-(benzoselenazole-2-yl)-2-bromoaniline,
2-bromo-4-(5-fluorobenzoselenazole-2-yl)aniline,
4-(5-fluorobenzoselenazole-2-yl)-2-methylaniline,
4-(5-fluorobenzoselenazole-2-yl)aniline,
2-bromo-4-(5-fluorobenzoselenazole-2-yl)-6-methylaniline,
4-(5-bromobenzoselenazole-2-yl)-2-chloroaniline,
2-methyl-4-(5-methylbenzoselenazole-2-yl)aniline,
2-methyl-4-[5-(trifluoromethyl)benzoselenazole-2-yl]aniline,
2-(3,4-dimethoxy-phenyl)-5-fluoro-benzoselenazole,
4-(6-ethoxybenzoselenazole-2-yl)-2-methylaniline,
4-(6-ethoxy-5-fluorobenzoselenazole-2-yl)-2-methylaniline,
5-(benzoselenazole-2-yl)-2-methoxyphenol,
2-(3,4-dimethoxyphenyl)benzoselenazole,
2-fluoro-4-(5-fluorobenzoselenazole-2-yl)aniline,
2-bromo-6-fluoro-4-(5-fluorobenzoselenazole-2-yl)aniline,
5-(5-fluorobenzoselenazole-2-yl)-2-methylaniline,
2-[3-chloro-4-(trifluoromethoxy)phenyl]-5-fluorobenzoselenazole,
4-(5-deuterobenzoselenazole-2-yl)-2-methylaniline,
2,6-difluoro-4-(5-fluorobenzoselenazole-2-yl)aniline,and
2-fluoro-4-(5-fluorobenzoselenazole-2-yl)-6-methylaniline.

The compounds of the present invention may be prepared by the following method:

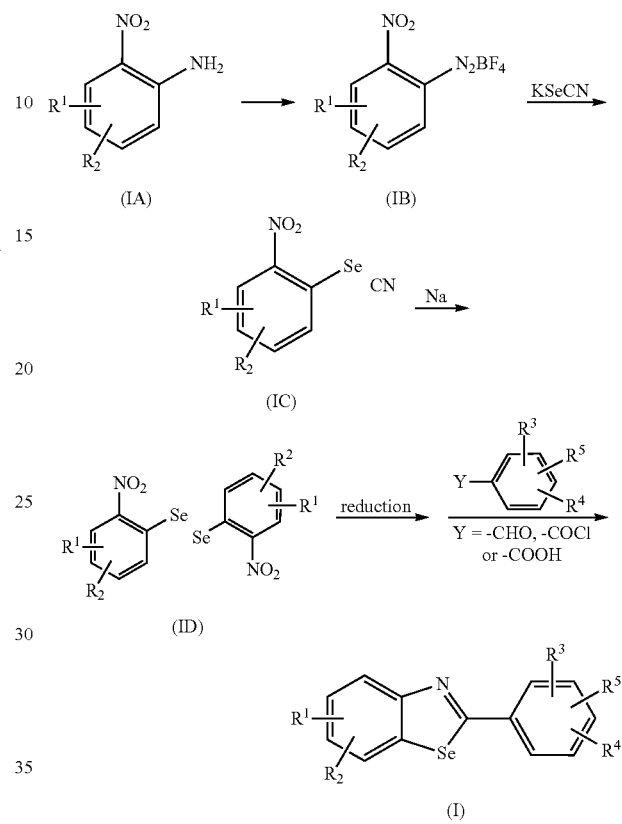

Corresponding diazoniumtetrafluoroborate (IB) was generated by the diazotization reaction between 2-nitroaniline compounds of formula (IA) and isoamyl nitrite in the presence of boron trifluoride diethyl etherate, the diazoniumtetrafluoroborate was then reacted with potassium selenocyanate to obtain phenyl selenocyanate compounds (IC), and the phenyl selenocyanate compounds were reacted in sodium/ethanol to obtain diselenium nitro compounds (ID). The compounds (ID) were reduced under certain conditions to obtain corresponding amino compounds, and the amino compounds were cyclized with corresponding benzaldehyde, benzoyl chloride or benzoic acid. The obtained benzoselenazole compounds may be end products, or may be subject to the reduction reaction, the halogenation reaction or other reactions to obtain corresponding target products (I). The groups $R^1$, $R^2$, $R^3$, $R^4$ and $R^5$ are as defined above.

The present invention further provides pharmaceutical compositions containing any one of the compounds of the present invention, pharmaceutically acceptable salts thereof or easily hydrolyzableprodrugs thereof as active components or main active components, supplemented by pharmaceutically acceptable adjuvants.

The compounds of the present invention, pharmaceutically acceptable salts thereof or easily hydrolyzableprodrugs thereof can be applied in the preparation of medicines for treating or preventing breast cancer.

Unless otherwise stated, the terms in the claims and the description are defined as below.

"Hydrogen" refers to protium (1H) which is a main stable isotope of hydrogen.

"Deuterium" is a stable isotope of hydrogen and also referred to as heavy hydrogen, and its symbol is D.

"Halogen" refers to fluorine atoms, chlorine atoms, bromine atoms or iodine atoms.

"Hydroxyl" refers to —OH.

"Cyano" refers to —CN.

"Nitro" refers to —$NO_2$.

"Alkyl" is a saturated aliphatic group having 1 to 10 carbon atoms, including a straight-chain group and a branched-chain group (the numerical range (e.g., 1 to 10) mentioned in the present application means that this group (alkyl in this case) may contain one carbon atom, two carbon atoms, three carbon atoms or even ten carbon atoms). An alkyl containing 1 to 4 carton atoms is a low-level alkyl. A low-level alkyl without any substituent group is an unsubstituted low-level alkyl, for example, methyl, ethyl, propyl, 2-propyl, n-butyl, isobutyl, tert-butyl or the like. The alkyl may be substituted or unsubstituted.

"Alkoxy" represents —O— (unsubstituted alkyl) and —O— (unsubstitutedalkoxy), and further represents —O— (unsubstituted alkyl).[User1] Representative embodiments include but are not limited to methoxy, ethoxy, propoxy, cyclopropoxy or the like.

"Pharmaceutically acceptable salts" include salts formed by the compounds of formula (I) with organic acids or inorganic acids, and represent salts maintaining the bioavailability and properties of the precursor compounds. These salts include:

(1) salts formed by the compounds with acids, which are obtained by reacting free bases of the precursor compounds with inorganic acids or organic acids, wherein the inorganic acids include (but not limited to): for example, hydrochloric acid, hydrobromic acid, nitric acid, phosphoric acid, meta phosphoric acid, sulfuric acid, sulfurous acid, perchloric acid and the like; the organic acids include (but not limited to): for example, acetic acid, propanoic acid, acrylic acid, oxalic acid, (D) or (L) malic acid, fumaric acid, maleic acid, hydroxybenzoic acid, γ-hydroxybutyric acid, methoxybenzoic acid, phthalic acid, methanesulfonic acid, ethanesulfonic acid, 1-naphthalenesulphonic acid, 2-naphthalenesulphonic acid, p-toluenesulfonic acid, salicylic acid, tartaric acid, citric acid, lactic acid, mandelic acid, succinic acid, malonic acid and the like; and (2) salts generated by substituting acidic protons in the precursor compounds with metal ions or coordinating the acidic protons in the precursor compounds with organic bases, wherein the metal ions include, for example, alkali metal ions, alkaline-earth metal ions or aluminum ions; and the organic bases include, for example, ethanolamine, diethanolamine, triethanolamine, trometamol, N-methylglucamine and the like.

"Pharmaceutical compositions" refer to mixtures of one or more of the compounds described herein or pharmaceutically acceptable salts thereof and prodrugs thereof with other chemical components, for example, pharmaceutically acceptable carriers and excipients. The pharmaceutical compositions are aimed at facilitating the administration of the compounds to a living body.

"Prodrugs" refer to compounds which have pharmacological action only after they are transformed into active compounds. The prodrugs themselves have no or low bioactivity, and will become active substances after in vivo metabolism. This process is to increase the bioavailability of medicines, enhance the targeting performance and reduce the toxicity and side effects of medicines.

The present invention further claims pharmaceutical compositions containing any one of the above-described compounds, pharmaceutically acceptable salts thereof or easily hydrolysable prodrug amides thereof and other pharmaceutically active components.

The present invention also encompasses any one of the above-described compounds, pharmaceutically acceptable salts thereof, easily hydrolysable prodrug amides thereof or isomers thereof. The present invention may be prepared into any clinically or pharmaceutically acceptable dosage form by the known methods in the art. For oral administration, the present invention may be prepared into conventional solid preparations such as tablets, capsules, pills or granules, or oral liquid preparations such as oral solution, oral suspension or syrup. During the preparation of oral preparations, proper filling agents, binding agents, disintegrating agents, lubricating agents and the like may be added. For parenteral administration, the present invention may be prepared into injection preparations such as injection solution, sterile powder for injection and concentrated solution for injection. During the preparation of injection preparations, existing conventional methods in the pharmaceutical field may be used. During the preparation of injection preparations, no or proper additives may be added, depending upon the properties of the medicines.

The compounds of the present invention have a novel 2-phenyl-benzoselenazole matrix-cycle structure, and provide new mechanisms and treatment plans for the treatment or prevention of the breast cancer. The compounds of the present invention have the following characteristics:

(1) the compounds of the present invention can effectively inhibitor reduce the growth or proliferation of breast cancer cells of mammals with tumors; and (2) the compounds of the present invention have better physicochemical properties, more remarkable pharmaceutical effect, low toxicity and low side effect.

DETAILED DESCRIPTION OF THE INVENTION

To make the objectives, technical schemes and advantages of the present invention clearer, the present invention will be further described below in details by specific implementations. It should be understood that the descriptions are merely exemplary and not intended to limit the scope of the present invention.

Synthesis Embodiments

Embodiment 1:

Synthesis of
4-(benzoselenazole-2-yl)-2-bromoaniline (7)

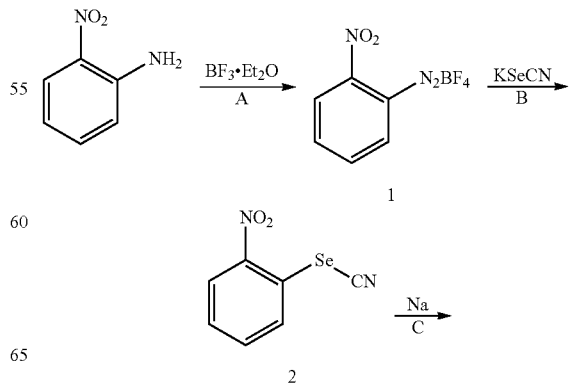

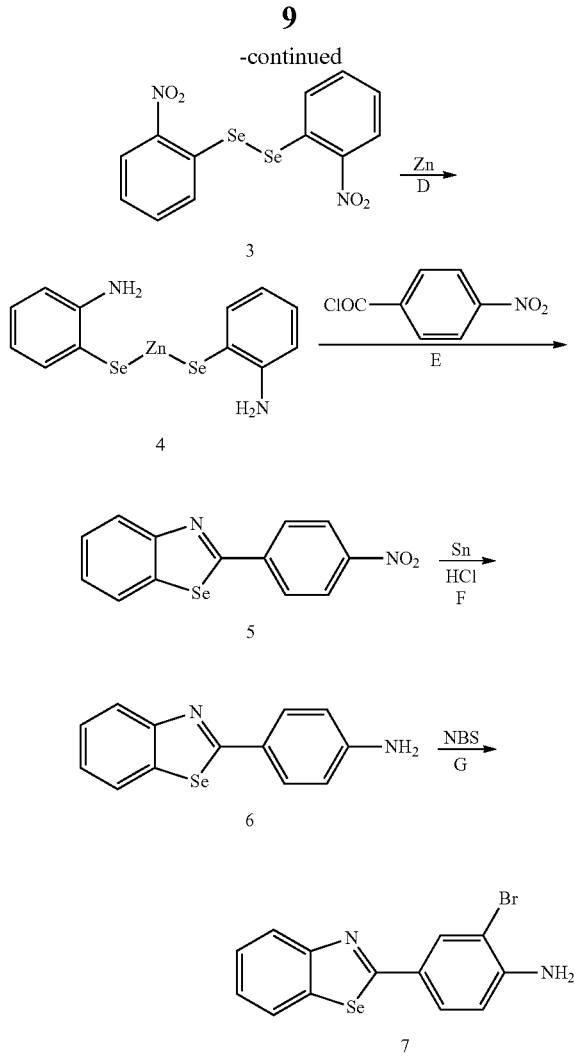

Step A: A solution of 2-nitroaniline(15.0 g, 108 mmol) in dichloromethane (150 mL) was added dropwise into boron trifluoride diethyl etherate (23.1 g, 163 mmol) at −10□ to −15□ and stirred for 15 min, and a solution of isoamyl nitrite (15.26 g, 130 mmol) in dichloromethane (75 mL) was added dropwise at this temperature. At the end of addition, the reaction mixture was continuously stirred for 30 minutes, and then stirred for 30 minutes at −10□ to 0□. The reaction system was added with cold petroleum ether (250 mL) dropwise and then filtered. The filter cake was washed with cold methyl tert-butyl ether (MTBE) (40 mL) to obtain 2-nitro-phenyl-diazonium tetrafluoroborate (1) (18.7 g). The yield was 73.1%.

Step B: A solution of potassium selenocyanate (8.0 g, 55.5 mmol) in water (80 mL) was added into a mixture of the compound 1 (13.0 g, 54.9 mmol) and water (300 mL) in an ice-water bath, and the reaction mixture was continuously stirred for 30 min at the end of addition. The reaction mixture was filtered, and the filter cake was washed with a small amount of water and then dried in vacuum at 60□ to obtain 1-nitro-2-phenyl selenocyanate (2) (11.2 g). The yield was 89.8%.

Step C: Sodium (6.0 g, 261 mmol) was added into a mixture of the compound 2 (10.5 g, 46.2 mol) and absolute ethyl alcohol (520 mL) at the room temperature, and the mixture was stirred for 1 h in a water bath. The reaction mixture was cooled to 0□ to 5□ and filtered, the filter cake was washed with a small amount of cold ethanol, and the collected solid was suspended in methylbenzene (100 mL), heated to reflux to dissolve the product, and filtered immediately. The filtrate was cooled to 0□ to 5□ to separate out solid and then filtered, and the filter cake was collected to obtain 1,2-di(2-nitrophenyl) diselenide (3) (4.5 g). The yield was 48.4%.

Step D: Zinc powder (13.5 g, 206 mmol) was added into a suspension solution of the compound 3 (4.5 g, 11.2 mmol) in acetic acid (90 mL) at 40□, and the reaction mixture was heated to 100□ and continuously stirred for 2 h. The reaction mixture was cooled below 50□, slowly added with 6M hydrochloric acid (40 mL) dropwise and filtered to remove insoluble substances. The filtrate was adjusted with 20% sodium acetate aqueous solution until the pH value was 2 to 3, and the solid was separated out. The reaction mixture was filtered, and the filter cake was dried to obtain di[(2-aminophenyl)seleno]zinc (4) (3.0 g). The yield was 77.8%.

Step E: A mixture of the compound 4 (3.6 g, 17.4 mmol) and 4-nitro-benzoyl chloride (4.77 g, 25.7 mmol) was stirred for 2 h at 110□. The mixture was cooled to the room temperature, added with saturated sodium bicarbonate aqueous solution (60 mL) and extracted with ethyl acetate (50 mL×3), and the combined organic phase was washed with saturated saline solution (20 mL) and dried with anhydrous sodium sulfate. The solvent was evaporated under reduced pressure, and the product was purified by chromatography (200 to 300 meshes of silica gel, elution with ethyl acetate: petroleum ether=1:5 to 3:1) to obtain 2-(4-nitrophenyl) benzoselenazole (5) (500 mg). The yield was 6.42%. $^1$H NMR (DMSO-d$_6$, 400 MHz) δ 8.40 (dd, J=2.0, 6.8 Hz, 2H), 8.21 (d, J=8.8 Hz, 2H), 7.76-7.74 (m, 1H), 7.36-7.33 (m, 2H), 7.27-7.23 (m, 1H).

Step F: The compound 5 (450 mg, 1.48 mmol) was dissolved into ethanol (10 mL) and then added with 2M hydrochloric acid (15 mL) and tin powder (2.25 g, 6.74 mmol), and the mixture was refluxed and stirred for 2 h. Most of the solvent was evaporated under reduced pressure, then added with water (15 mL), adjusted with dilute sodium hydroxide solution until the pH value was 9 to 10, extracted with dichloromethane (20 mL×3), and dried with anhydrous sodium sulfate. The solvent was evaporated under reduced pressure, and the product was purified by chromatography (200 to 300 meshes of silica gel, elution with ethyl acetate: petroleum ether=1:15 to 1:4) to obtain 4-(benzoselenazole-2-yl)aniline (6) (300 mg). The yield was 74.2%. $^1$H NMR (DMSO-d$_6$, 400 MHz) δ 8.07 (dd, J=0.8, 8.0 Hz, 1H), 7.89 (dd, J=0.8, 8.0 Hz, 1H), 7.72-7.69 (m, 2H), 7.46-7.42 (m, 1H), 7.28-7.23 (m, 1H), 6.66-6.63 (m, 2H), 5.92 (s, 2H).

Step G: A solution of NBS (117 mg, 0.657 mmol) in dichloromethane (15 mL) was added dropwise into a solution of the compound 6 (200 mg, 0.732 mmol) in dichloromethane (5 mL) at −10□, and the mixture was continuously stirred for 0.5 h at this temperature at the end of addition. The reaction mixture was washed with water (10 mL) and dried with anhydrous sodium sulfate. The solvent was evaporated under reduced pressure, and the product was purified by chromatography (200 to 300 meshes of silica gel, elution with ethyl acetate: petroleum ether=1:10) to obtain 4-(benzoselenazole-2-yl)-2-bromoaniline (7) (179 mg). The yield was 69.5%. $^1$H NMR (DMSO-d$_6$, 400 MHz) δ 8.10 (dd, J=1.0, 8.0 Hz, 1H), 8.02 (d, J=1.0 Hz, 1H), 7.94 (dd, J=1.0, 8.0 Hz, 1H), 7.72 (dd, J=1.0, 8.0 Hz, 1H), 7.49-7.45 (m, 1H), 7.31-7.27 (m, 1H), 6.88 (d, J=8.4 Hz, 1H), 6.11 (s, 2H). MS (EI, m/z):350.9 [M−H]$^-$.

Embodiment 2:

Synthesis of 4-(5-fluorobenzoselenazole-2-yl)aniline (13) and 2-bromo-4-(5-fluorobenzoselenazole-2-yl) aniline (14)

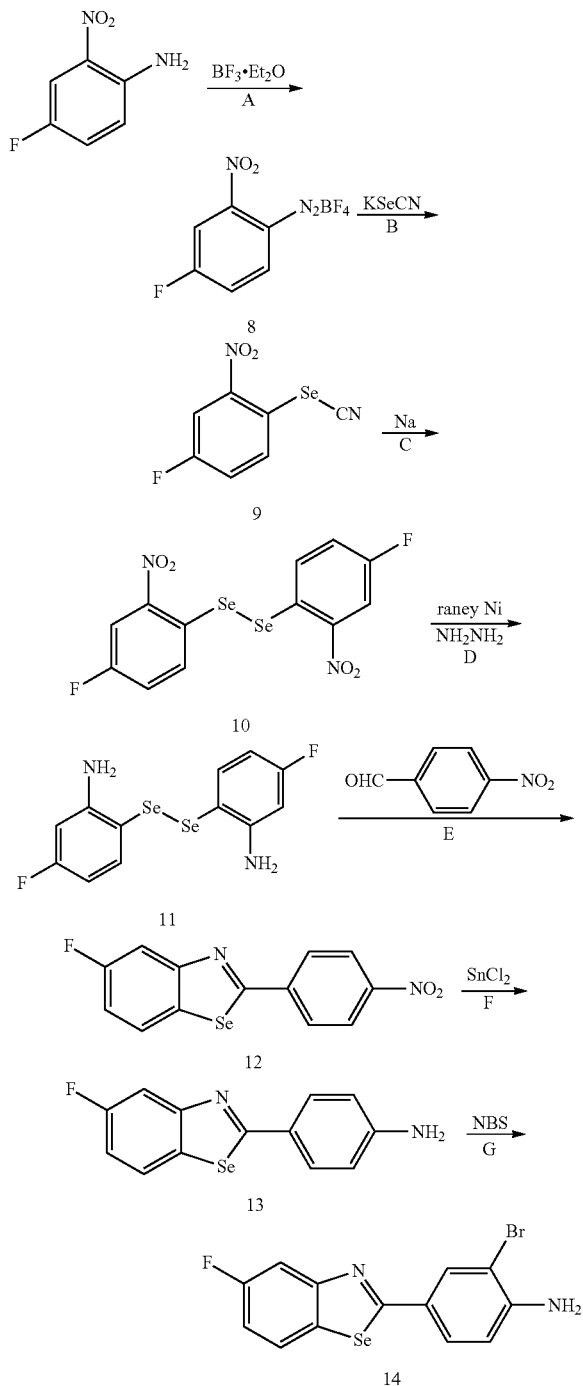

Step A: A solution of 2-nitro-4-fluoroaniline (5.0 g, 32.0 mmol) in dichloromethane (50 mL) was added dropwise into boron trifluoride diethyl etherate (6.8 g, 47.9 mmol) at −10□ to −15□ and stirred for 15 min, and a solution of isoamyl nitrite (4.5 g, 38.4 mmol) in dichloromethane (25 mL) was added dropwise at this temperature. At the end of addition, the mixture was continuously stirred for 30 minutes, and then stirred for 30 minutes at −10□ to 0□. The reaction mixture was added with cooled petroleum ether (80 mL) dropwise and then filtered. The filter cake was washed with cold MTBE (10 mL) to obtain 2-nitro-4-fluorophenyl-diazonium tetrafluoroborate (8) (13.0 g). The compound was directly used in the next reaction without purification.

Step B: A solution of potassium selenocyanate (4.84 g, 33.6 mmol) in water (30 mL) was added into a mixture of the crude compound 8 (13.0 g) and water (170 mL) in an ice-water bath, and the reaction mixture was continuously stirred for 20 min at the end of addition. The reaction mixture was filtered, and the filter cake was washed with a small amount of water and then dried in vacuum at 60□ to obtain 4-fluoro-2-nitro-1-phenyl selenocyanate (9) (9.1 g). The compound was directly used in the next reaction without purification.

Step C: Sodium (4.1 g, 178 mmol) was added into a mixture of the crude compound 9 (9.1 g) and absolute ethyl alcohol (300 mL) at the room temperature, and the mixture was stirred for 1 h in a water bath. The mixture was cooled to 0□ to 5□ and filtered, and the filter cake was washed with a small amount of cold ethanol. The collected solid was suspended in methylbenzene (80 mL), heated to reflux to dissolve the product, and filtered immediately. The filtrate was cooled to 0□ to 5□ to separate out solid and then filtered, and the filter cake was collected to obtain 1,2-di(4-fluoro-2-nitrophenyl)diselenide (10) (2.0 g). The total yield of the reactions in the steps A, B and C was 21.9%.

Step D: The compound 10 (1.49 g, 3.4 mmol) and raney nickel (1.2 g) were suspended in isopropanol (30 mL), 85% hydrazine hydrate (1.8 mL) was added, and the mixture was heated to reflux and continuously stirred for 2.5 h. The mixture was immediately filtered through a celite pad, the filter cake was washed with a small amount of isopropanol, and the filtrate was collected. The solvent was evaporated under reduced pressure, and the product was purified by chromatography (200 to 300 meshes of silica gel, elution with ethyl acetate: petroleum ether=1:10 to 1:5) to obtain 6,6'-diselenodi(3-fluoroaniline) (11) (370 mg). The yield was 28.8%.

Step E: A mixture containing the compound 11 (370 mg, 0.978 mmol), 4-nitrobenzaldehyde (296 mg, 1.958 mmol), sodium metabisulfite (372 mg, 1.956 mmol) and anhydrous DMSO (15 mL) was stirred for 72 h under nitrogen at 120□. The mixture was cooled to the room temperature, added with saturated ammonium chloride aqueous solution (60 mL), extracted with ethyl acetate (25 mL×3), and dried with anhydrous sodium sulfate. The solvent was evaporated under reduced pressure, and the product was purified under reduced pressure by chromatography (200 to 300 meshes of silica gel, elution with ethyl acetate: petroleum ether=1:50) to obtain 5-fluoro-2-(4-nitrophenyl)benzoselenazole (12) (76 mg). The yield was 12.1%. $^1$H NMR (DMSO-$d_6$, 300 MHz) δ 8.39-8.28 (m, 5H), 8.01 (dd, J=2.4, 9.9 Hz, 1H), 7.41-7.34 (m, 1H).

Step F: The compound 12 (70 mg, 0.218 mmol) was dissolved into ethanol (5 mL) and then added with stannous chloride hydrate (246 mg, 1.09 mmol), and the mixture was refluxed and stirred for 5 h. The mixture was cooled to the room temperature, added with saturated saline solution (20 mL), extracted with ethyl acetate (25 mL×3), and dried with anhydrous sodium sulfate. The solvent was evaporated under reduced pressure, and the product was purified by chromatography (200 to 300 meshes of silica gel, elution with ethyl acetate: petroleum ether=1:15 to 1:5) to obtain 4-(5-fluorobenzoselenazole-2-yl)aniline (13) (50 mg). The yield was 78.8%, MS (EI, m/z):291.0 [M−H]⁻.

Step G: A solution of NBS (29.6 mg, 0.166 mmol) in dichloromethane (40 mL) was added dropwise into a solution of the compound 13 (44 mg, 0.151 mmol) in dichloromethane (40 mL) in an ice-salt bath, and the mixture was continuously stirred for 10 min at this temperature at the end of addition. The reaction mixture was washed with water (20 mL×2) and dried with anhydrous sodium sulfate. The solvent was evaporated under reduced pressure, and the product was purified by chromatography (200 to 300 meshes of silica gel, elution with ethyl acetate: petroleum ether=1:20) to obtain 2-bromo-4-(5-fluorobenzoselenazole-2-yl)aniline (14). 1H NMR (DMSO-d6, 300 MHz) δ 8.14-8.09 (m, 1H), 8.03 (d, J=1.8 Hz, 1H), 7.78-7.70 (m, 2H), 7.23-7.16 (m, 1H), 6.87 (d, J=8.4 Hz, 1H), 6.14 (s, 2H). MS (EI, m/z): 369.0 [M−H]⁻.

Embodiment 3:

Synthesis of 4-(5-fluorobenzoselenazole-2-yl)-2-methylaniline (17)

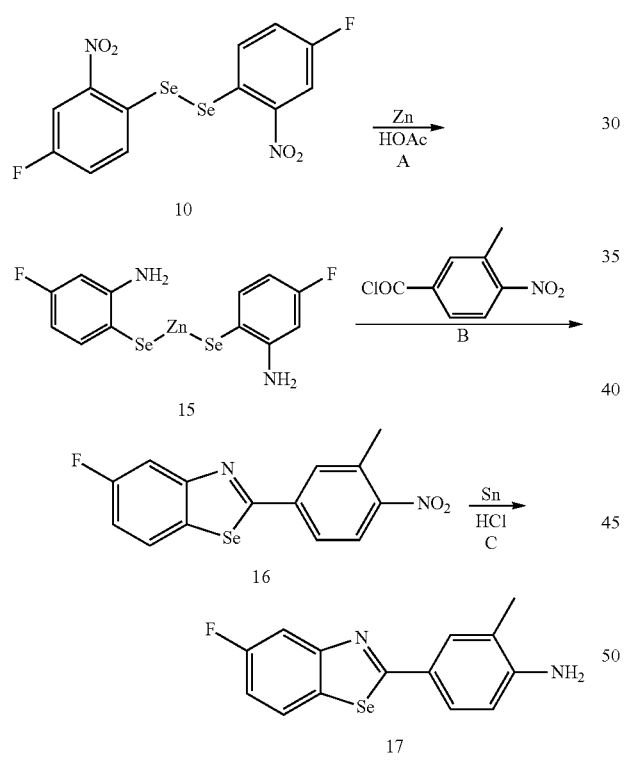

Step A: Zinc powder (5.5 g, 84.1 mmol) was added into a suspension of the compound 10 (2.0 g, 4.57 mmol) in acetic acid (40 mL) at 40□, then heated to 100□ and continuously stirred for 3 h. The reaction mixture was cooled below 50□, slowly added with 6M hydrochloric acid (40 mL) and filtered to remove insoluble substances. The filtrate was adjusted with 20% sodium acetate until the pH value was 2 to 3, and the solid was collected by filtration and dried to obtain di[(2-amino-4-fluorophenyl)seleno]zinc (15) (1.2 g). The yield was 61.9%.

Step B: A mixture of the compound 15 (590 mg, 3.10 mmol) and 3-methyl-4-nitrobenzoyl chloride (663 mg, 3.32 mmol) was stirred for 4 h at 100□. The mixture was cooled to the room temperature, added with saturated sodium bicarbonate aqueous solution (15 mL) and extracted with ethyl acetate (30 mL×2). The combined organic phase was washed with saturated saline solution (10 mL) and dried with anhydrous sodium sulfate. The solvent was evaporated under reduced pressure, and the product was purified by chromatography (200 to 300 meshes of silica gel, elution with ethyl acetate: petroleum ether=1:15 to 1:1) to obtain 5-fluoro-2-(3-methyl-4-nitrophenyl)benzoselenazole (16) (750 mg). The yield was 72.2%. ¹H NMR (DMSO-d₆, 300 MHz) δ 8.32-8.27 (m, 1H), 8.19-8.13 (m, 3H), 7.98 (dd, J=2.4, 9.9 Hz, 1H), 7.40-7.33 (m, 1H), 2.64 (s, 3H).

Step C: The compound 16 (200 mg, 0.597 mmol) was dissolved into ethanol (5 mL) and then added with 3M hydrochloric acid (4 mL) and tin powder (800 mg, 6.74 mmol), and the mixture was refluxed and stirred for 1.5 h. Most of the solvent was evaporated under reduced pressure, then added with water (15 mL), adjusted with dilute sodium hydroxide solution until the pH value was 9 to 10, extracted with ethyl acetate (20 mL×2), and dried with anhydrous sodium sulfate. The solvent was evaporated under reduced pressure, and the product was purified by chromatography (200 to 300 meshes of silica gel, elution with ethyl acetate: petroleum ether=1:15 to 1:4) to obtain 4-(5-fluorobenzoselenazole-2-yl)-2-methylaniline (17) (103 mg). The yield was 56.4%. ¹H NMR (DMSO-d₆, 400 MHz) δ 8.08-8.05 (m, 1H), 7.72-7.69 (m, 1H), 7.62-7.57 (m, 2H), 7.18-7.13 (m, 1H), 6.68 (d, J=8.4 Hz, 1H), 5.75 (s, 2H), 2.14 (s, 3H). MS (EI, m/z):305.0 [M−H]⁻.

Embodiment 4:

Synthesis of 2-bromo-4-(5-fluorobenzoselenazole-2-yl)-6-methylaniline (18)

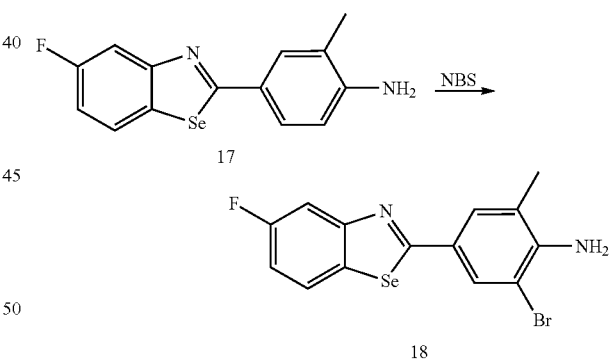

NBS (57 mg, 0.320 mmol) was added into a solution of the compound 17 (88 mg, 0.229 mmol) in DMF (5 mL) at the room temperature, and the mixture was continuously stirred for 20 min at this temperature at the end of addition. The mixture was added with water (25 mL) and extracted with ethyl acetate (20 mL×2), and the combined organic phase was washed with saturated sodium bicarbonate aqueous solution (10 mL) and dried with anhydrous sodium sulfate. The solvent was evaporated under reduced pressure, and the product was purified by chromatography (200 to 300 meshes of silica gel, elution with ethyl acetate: petroleum ether=1:5) to obtain 2-bromo-4-(5-fluorobenzoselenazole-2-yl)-6-methylaniline (18) (73 mg). The yield was 83.0%. ¹H NMR (DMSO-d₆, 500 MHz) δ 8.13-8.10 (m, 1H), 7.92 (d, J=2.0 Hz, 1H), 7.77-7.74 (m, 1H), 7.64 (s, 1H), 7.21-7.17 (m, 1H), 5.76 (s, 2H), 2.26 (s, 3H). MS (El, m/z):384.9 [M+H]⁺.

Embodiment 5:

Synthesis of 4-(5-bromobenzoselenazole-2-yl)-2-chloroaniline (25)

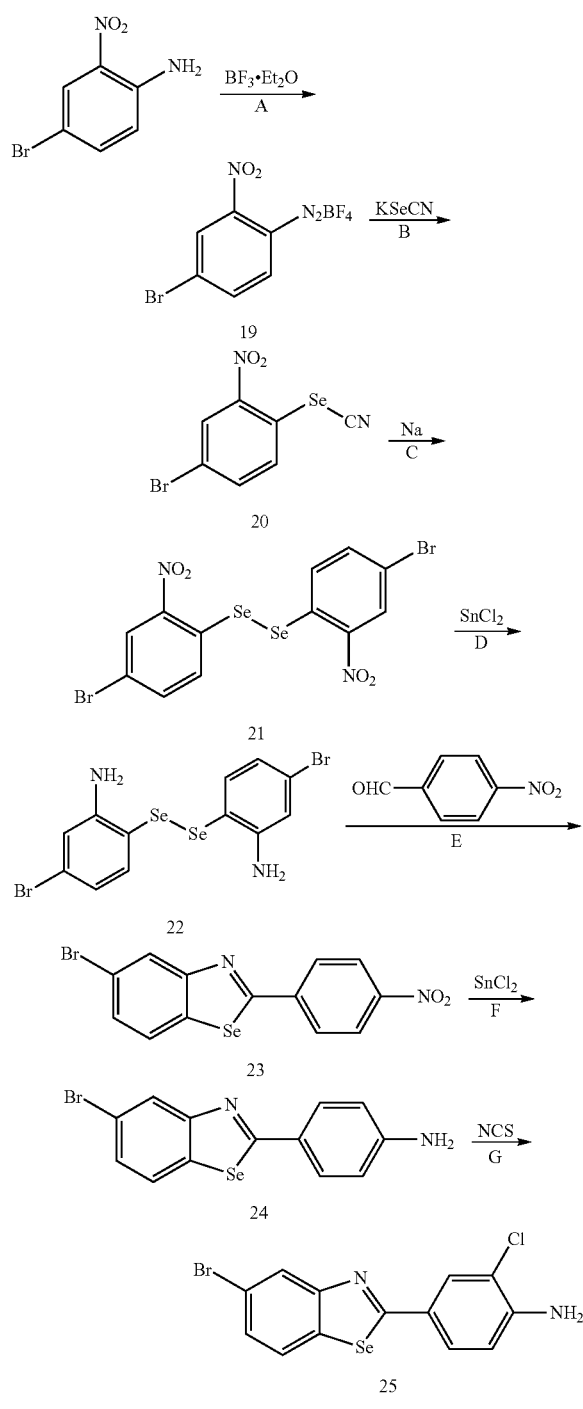

The steps A, B and C referred to the steps A, B and C in Embodiment 2.

Step D: The compound 21 (1.9 g, 3.393 mmol) was dissolved into ethanol (40 mL) and then added with stannous chloride hydrate (3.8 g, 16.84 mmol), and the mixture was refluxed and stirred for 3.5 h under nitrogen. The mixture was cooled to the room temperature, added with saturated saline solution (20 mL), extracted with ethyl acetate (25 mL×3), and dried with anhydrous sodium sulfate. The solvent was evaporated under reduced pressure, and the product was purified by chromatography (200 to 300 meshes of silica gel, elution with ethyl acetate: petroleum ether=1:10) to obtain 6,6'-diselenodi(3-bromoaniline) (22) (450 mg). The yield was 26.5%.

Step E: Referring to the step E in Embodiment 2, to get 5-bromo-2-(4-nitrophenyl)benzoselenazole (23). ¹H NMR (DMSO-d₆, 300 MHz) δ 8.39-8.30 (m, 5H), 8.23 (d, J=9.0 Hz, 1H), 7.61 (d, J=9.0 Hz, 1H).

Steps F and G: Referring to the step F in Embodiment 2 to get compound 24. The compound 23 was reduced to obtain a compound 24. The compound 24 (80 mg, 0.227 mmol) was dissolved into DMF (5 mL) and added with NCS (34 mg, 0.255 mmol), and the mixture was stirred overnight at the room temperature. The mixture was added with water (25 mL) and extracted with ethyl acetate (15 mL×3), and the combined organic phase was washed with saturated sodium bicarbonate aqueous solution (10 mL) and dried with anhydrous sodium sulfate. The solvent was evaporated under reduced pressure, and the product was purified by chromatography (200 to 300 meshes of silica gel, elution with ethyl acetate: petroleum ether=1:15) to obtain 4-(5-bromobenzoselenazole-2-yl)-2-chloroaniline (25). ¹H NMR (DMSO-d₆, 300 MHz) δ 8.10-8.04 (m, 2H), 7.87 (s, 1H), 7.68 (d, J=9.0 Hz, 1H), 7.43 (d, J=9.0 Hz, 1H), 6.88 (d, J=9.0 Hz, 1H), 6.16 (s, 2H). MS (El, m/z):384.9 [M−H]⁻.

Embodiment 6:

Synthesis of 2-methyl-4-(5-methylbenzoselenazole-2-yl)aniline (26)

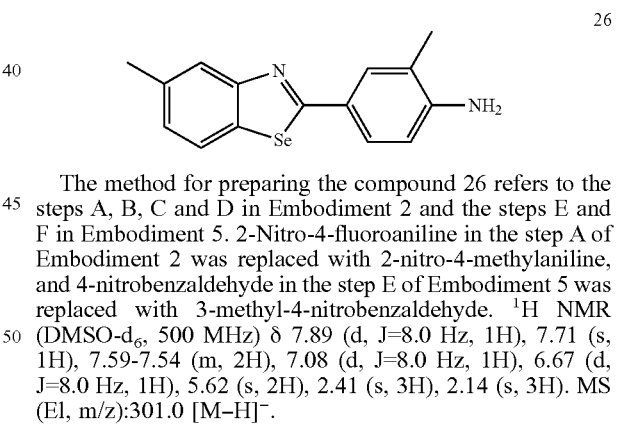

The method for preparing the compound 26 refers to the steps A, B, C and D in Embodiment 2 and the steps E and F in Embodiment 5. 2-Nitro-4-fluoroaniline in the step A of Embodiment 2 was replaced with 2-nitro-4-methylaniline, and 4-nitrobenzaldehyde in the step E of Embodiment 5 was replaced with 3-methyl-4-nitrobenzaldehyde. ¹H NMR (DMSO-d₆, 500 MHz) δ 7.89 (d, J=8.0 Hz, 1H), 7.71 (s, 1H), 7.59-7.54 (m, 2H), 7.08 (d, J=8.0 Hz, 1H), 6.67 (d, J=8.0 Hz, 1H), 5.62 (s, 2H), 2.41 (s, 3H), 2.14 (s, 3H). MS (El, m/z):301.0 [M−H]⁻.

Embodiment 7:

Synthesis of 2-methyl-4-[5-(trifluoromethyl)benzoselenazole-2-yl]aniline (27)

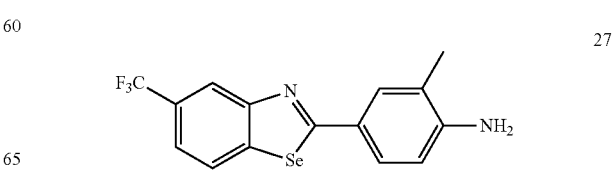

The method for preparing the compound 27 refers to the steps A, B, C and D in Embodiment 2 and the steps E and F in Embodiment 5. 2-nitro-4-fluoroaniline in the step A of Embodiment 2 was replaced with 2-nitro-4-trifluoromethylaniline, and 4-nitrobenzaldehyde in the step E of Embodiment 5 was replaced with 3-methyl-4-nitrobenzaldehyde. ¹H NMR (DMSO-d₆, 500 MHz) δ 8.31 (d, J=8.0 Hz, 1H), 8.16 (s, 1H), 7.65-7.62 (m, 2H), 7.55 (d, J=8.5 Hz, 1H), 6.70 (d, J=8.5 Hz, 1H), 5.77 (s, 2H), 2.15 (s, 3H). MS (El, m/z):355.0 [M−H]⁻.

Embodiment 8:

Synthesis of 2-(3,4-dimethoxy-phenyl)-5-fluoro-benzoselenazole (28)

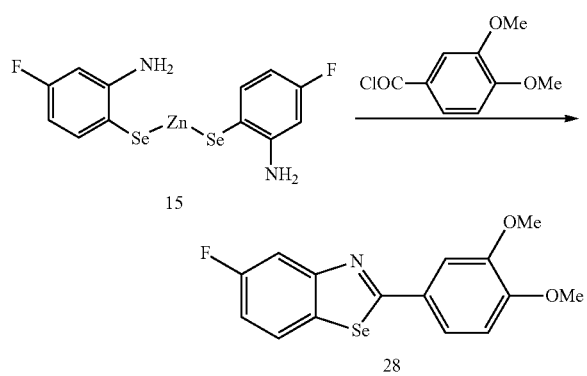

The method for preparing the compound 28 refers to the step B in Embodiment 3, wherein acyl chloride in the reaction equation was prepared by reacting a corresponding acid with thionyl chloride. MS (El, m/z):338.1 [M+H]⁺.

Embodiment 9:

Synthesis of 4-(6-ethoxybenzoselenazole-2-yl)-2-methylaniline (29)

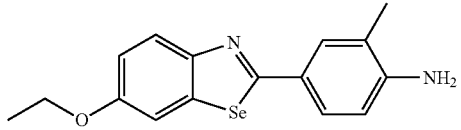

The method for preparing the compound 29 refers to the steps A, B, C and D in Embodiment 2 and the steps E and F in Embodiment 5. 2-nitro-4-fluoroaniline in the step A was replaced with 2-nitro-5-fluoroaniline, and 3-methyl-4-nitrobenzaldehyde in the step E of Embodiment 5 was replaced with 3-methyl-4-nitrobenzaldehyde. In the reduction reactions in the steps C and F, the solvent was ethanol so that F at the sixth site of benzaldehyde was substituted with ethoxy. The final resulting product was 4-(6-ethoxy-benzoselenazole-2-yl)-2-methylaniline (29). ¹H NMR (DMSO-d₆, 300 MHz) δ 7.76 (d, J=8.7 Hz, 1H), 7.63 (s, 1H), 7.55-7.50 (m, 2H), 6.99 (d, J=8.1 Hz, 1H), 6.66 (d, J=8.1 Hz, 1H), 5.58 (s, 2H), 4.09 (q, J=6.6 Hz, 2H), 2.13 (s, 3H), 1.35 (t, J=6.6 Hz, 3H). MS (El, m/z):333.0 [M+H]⁺.

Embodiment 10:

Synthesis of 4-(6-ethoxy-5-fluorobenzoselenazole-2-yl)-2-methylaniline (30)

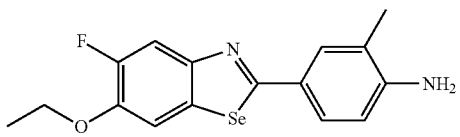

The method for preparing the compound 30 refers to the steps A, B, C and D in Embodiment 2 and the steps E and F in Embodiment 5. 2-nitro-4-fluoroaniline in the step A of Embodiment 2 was replaced with 2-nitro-4,5-difluoroaniline, and 4-nitrobenzaldehyde in the step E of Embodiment 5 was replaced with 3-methyl-4-nitrobenzaldehyde. In the reduction reactions in the steps C and F, the solvent was ethanol so that F at the sixth site of benzaldehyde was substituted with ethoxy. The final resulting product was 4-(6-ethoxy-5-fluorobenzoselenazole-2-yl)-2-methylaniline (30). ¹H NMR (DMSO-d₆, 300 MHz) δ 7.85 (d, J=8.4 Hz, 1H), 7.72 (d, J=12.0 Hz, 1H), 7.55-7.50 (m, 2H), 6.66 (d, J=8.1 Hz, 1H), 5.61 (s, 2H), 4.16 (q, J=6.9 Hz, 2H), 2.13 (s, 3H), 1.38 (t, J=6.9 Hz, 3H). MS (El, m/z):351.0 [M+H]⁺.

Embodiment 11:

Synthesis of 5-(benzoselenazole-2-yl)-2-methoxyphenol (32)

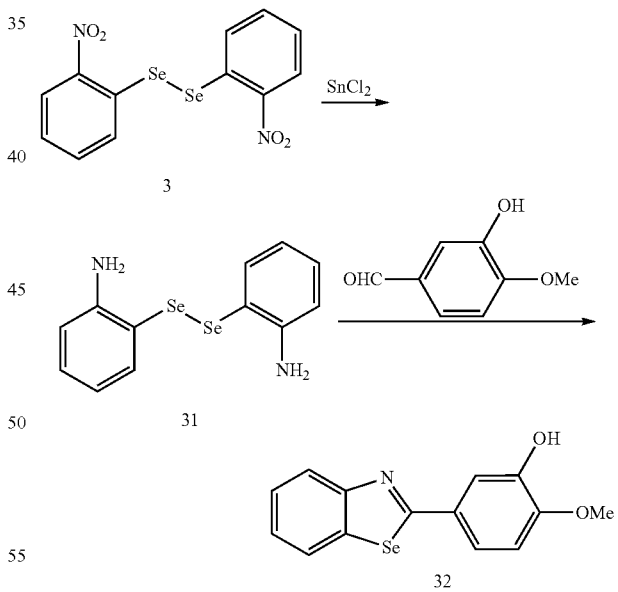

According to the step D in Embodiment 5 and the step E in Embodiment 2, compound 32 was synthesized as the aimed product while using compound 3 and 4-nitrobenzaldehyde as the starting materials. The compound 3 was used as raw material, and the method for preparing the compound 32 refers to the step D in Embodiment 5 and the step E in Embodiment 2. 4-nitrobenzaldehyde in the step E of Embodiment 2 was replaced with 3-hydroxyl-4-methoxybenzaldehyde. ¹H NMR (DMSO-d₆, 300 MHz) δ 9.55 (s, 1H), 8.13 (d, J=7.5 Hz, 1H), 7.99 (d, J=7.5 Hz, 1H), 7.51-7.44 (m, 3H), 7.36-7.30 (m, 1H), 7.06 (d, J=8.4 Hz, 1H), 3.85 (s, 3H). MS (El, m/z):306.0 [M+H]⁺.

Embodiment 12:

Synthesis of 2-(3,4-dimethoxyphenyl)benzoselenazole (33)

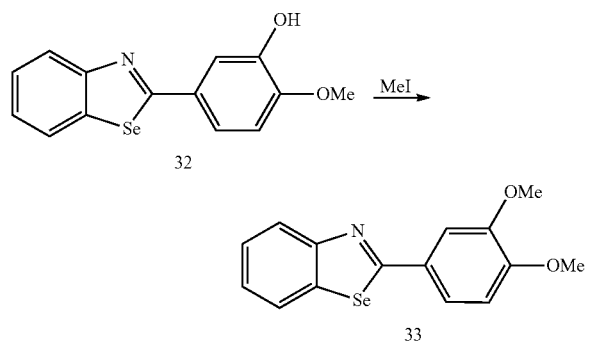

A mixture of the compound 32 (90 mg, 0.296 mmol), potassium carbonate (61 mg, 0.441 mmol), iodomethane (126 mg, 0.888 mmol) and DMF (8 mL) was stirred overnight at 50□. The mixture was added with water (40 mL) and extracted with ethyl acetate (20 mL×3), and the combined organic phase was washed with saturated saline solution (15 mL×2) and dried with anhydrous sodium sulfate. The solvent was evaporated under reduced pressure, and the product was purified by chromatography (200 to 300 meshes of silica gel, elution with ethyl acetate: petroleum ether=1:5) to obtain 2-(3,4-dimethoxy- phenyl)benzoselenazole (33). ¹H NMR (DMSO-d₆, 300 MHz) δ 8.13 (d, J=7.8 Hz, 1H), 8.02 (d, J=7.8 Hz, 1H), 7.60-7.55 (m, 2H), 7.52-7.47 (m, 1H), 7.36-7.31 (m, 1H), 7.10 (d, J=8.1 Hz, 1H), 3.89 (s, 3H), 3.85 (s, 3H). MS (El, m/z):320.0 [M+H]⁺.

Embodiment 13:

Synthesis of 2-fluoro-4-(5-fluorobenzoselenazole-2-yl)aniline (34) and 2-bromo-6-fluoro-4-(5-fluorobenzoselenazole-2-yl)aniline (35)

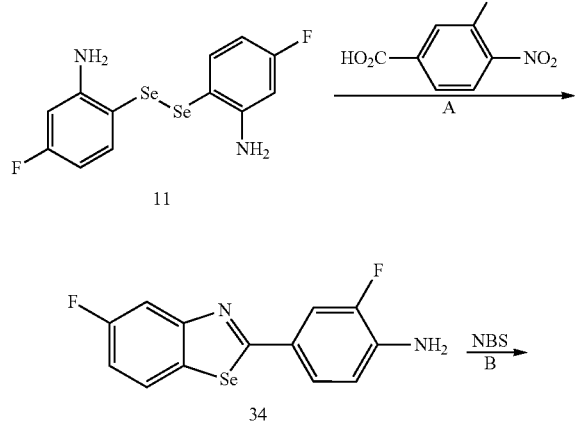

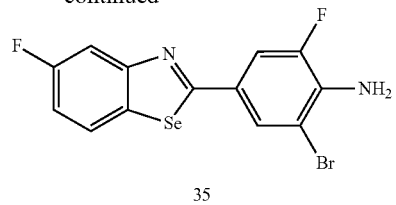

Step A: Tributylphosphine (1.28 g, 6.33 mmol) was added into a solution of the compound 11 (800 mg, 2.12 mmol) in methylbenzene (15 mL), then stirred for 5 min under nitrogen. To the mixture was added 3-fluoro-4-nitrobenzoic acid (392 mg, 2.12 mmol), and the resulting mixture was refluxed for 48 h under nitrogen. The mixture was cooled to the room temperature, added with water (25 mL) and adjusted with saturated sodium carbonate solution until the pH value was 9 to 10. The mixture was extracted with ethyl acetate (20 mL×3), and the combined organic phase was washed with saturated saline solution (15 mL) and dried with anhydrous sodium sulfate. The solvent was evaporated under reduced pressure, and the product was purified by chromatography (200 to 300 meshes of silica gel, elution with ethyl acetate: petroleum ether=1:15) to obtain 2-fluoro-4-(5-fluoro- benzoselenazole-2-yl)aniline (34). ¹H NMR (DMSO-d₆, 300 MHz) δ 8.13-8.09 (m, 1H), 7.77-7.73 (m, 1H), 7.69-7.64 (m, 1H), 7.59-7.56 (m, 1H), 7.22-7.16 (m, 1H), 6.88-6.83 (m, 1H), 6.00 (s, 2H). MS (El, m/z):309.0 [M-H]⁻.

Step B: 2-bromo-6-fluoro-(5-fluorobenzoselenazole-2-yl) aniline (35) was prepared by using the compound 34 as raw material, and the method refers to the step G in Embodiment 2. ¹H NMR (DMSO-d₆, 500 MHz) δ 8.16-8.13 (m, 1H), 7.90 (s, 1H), 7.79 (dd, J=2.0, 10.0 Hz, 1H), 7.73 (dd, J=2.0, 10.0 Hz, 1H), 7.24-7.20 (m, 1H), 6.12 (s, 2H). MS (El, m/z): 388.9 [M+H]⁺.

Embodiment 14:

Synthesis of 5-(5-fluorobenzoselenazole-2-yl)-2-methylaniline (37)

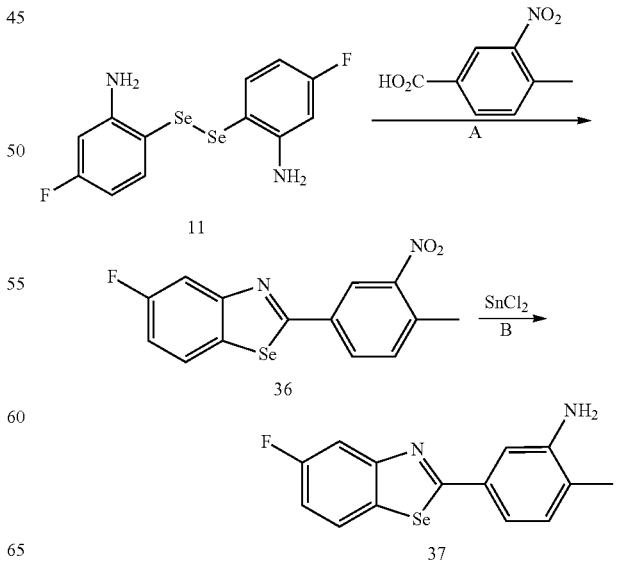

Step A: A solution of the compound 11 (800 mg, 2.12 mmol) and tributylphosphine (1.28 g, 6.32 mmol) in methylbenzene (15 mL) was stirred for 5 min under nitrogen and added with 3-nitro-4-methylbenzoic acid (380 mg, 2.09 mmol), and the mixture was refluxed and stirred for 48 h under nitrogen. The mixture was cooled to the room temperature, added with water (30 mL) and adjusted with 2M sodium hydroxide solution until the pH value was 9 to 10. The mixture was extracted with ethyl acetate (20 mL×3) and dried with anhydrous sodium sulfate. The solvent was evaporated under reduced pressure, and the product was purified by chromatography (200 to 300 meshes of silica gel, elution with ethyl acetate: petroleum ether=1:20 to 1:2) to obtain 5-fluoro-2-(4-methyl-3-nitrophenyl)benzoselenazole (36) (107 mg). The yield was 15.3%.

Step B: 5-(5-fluorobenzoselenazole-2-yl)-2-methylaniline (37) was prepared by using the compound 36 as raw material, and the experimental operation refers to the step F in Embodiment 2. $^1$H NMR (DMSO-d$_6$, 500 MHz) δ 8.17-8.14 (m, 1H), 7.82 (dd, J=2.5, 10.0 Hz, 1H), 7.38 (s, 1H), 7.27-7.23 (m, 1H), 7.18 (d, J=8.0 Hz, 1H), 7.10 (d, J=8.0 Hz, 1H), 2.13 (s, 3H). MS (El, m/z):305.1 [M−H]$^-$.

Embodiment 15:

Synthesis of 2-[3-chloro-4-(trifluoromethoxy)phenyl)-5-fluorobenzoselenazole (38)

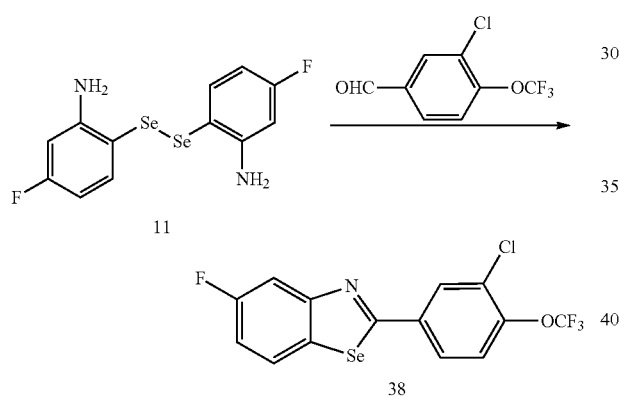

The method for preparing the compound 38 refers to the step E in Embodiment 2, wherein 4-nitrobenzaldehyde in the step E of Embodiment 2 was replaced with 3-chloro-4 (trifluoromethoxy)benzaldehyde. $^1$H NMR (DMSO-d$_6$, 300 MHz) δ 8.35 (d, J=1.2 Hz, 1H), 8.30-8.27 (m, 1H), 8.17-8.15 (m, 1H), 7.98-7.96 (m, 1H), 7.77-7.75 (m, 1H), 7.38-7.34 (m, 1H). MS (El, m/z):394.0 [M−H]$^-$.

Embodiment 16:

Synthesis of 4-(5-deuterobenzoselenazole-2-yl)-2-methylaniline (40)

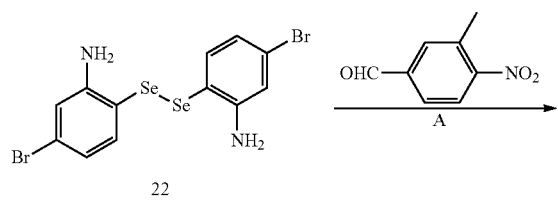

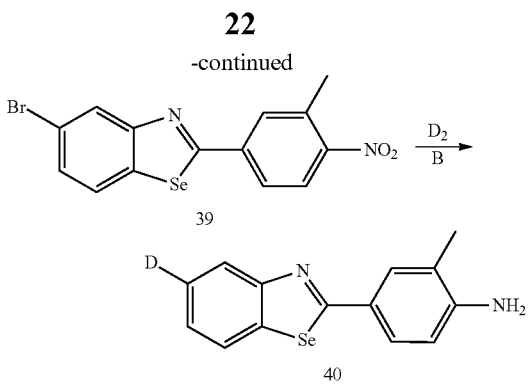

Step A: The compound 22 and 3-methyl-4-nitrobenzaldehyde were used as raw materials, and the experimental operation of preparing the compound 39 refers to the step E in Embodiment 2. $^1$H NMR (DMSO-d$_6$, 400 MHz) δ 8.35 (s, 1H), 8.24 (d, J=8.4 Hz, 1H), 8.19 (s, 1H), 8.15-8.14 (m, 2H), 7.62 (dd, J=2.0, 8.4 Hz, 1H), 2.65 (s, 3H).

Step B: The compound 39 (42 mg, 0.106 mmol) was suspended in DMF (5 mL) and then added with deuteroxide (0.5 mL) and 5% palladium carbon, and the mixture was stirred overnight under deuterium gas at the normal pressure. The mixture was filtered through a celite pad, added with water (20 mL) and extracted with ethyl acetate (20 mL×2), and the combined organic phase was washed with saturated saline solution (10 mL×2) and dried with anhydrous sodium sulfate. The solvent was evaporated under reduced pressure, and the product was purified by chromatography (200 to 300 meshes of silica gel, elution with ethyl acetate: petroleum ether=1:10) to obtain 4-(5-deuterobenzoselenazole-2-yl)-2-methylaniline (40). $^1$H NMR (DMSO-d$_6$, 400 MHz) δ 8.06-8.02 (m, 2H), 7.62-7.59 (m, 2H), 8.16 (dd, J=2.0, 8.8 Hz, 1H), 6.68 (d, J=8.0 Hz, 1H), 5.78 (s, 2H), 2.14 (s, 3H). MS (El, m/z):288.0 [M−H]$^-$.

Embodiment 17:

Synthesis of 2,6-difluoro-4-(5-fluorobenzoselenazole-2-yl)aniline (41)

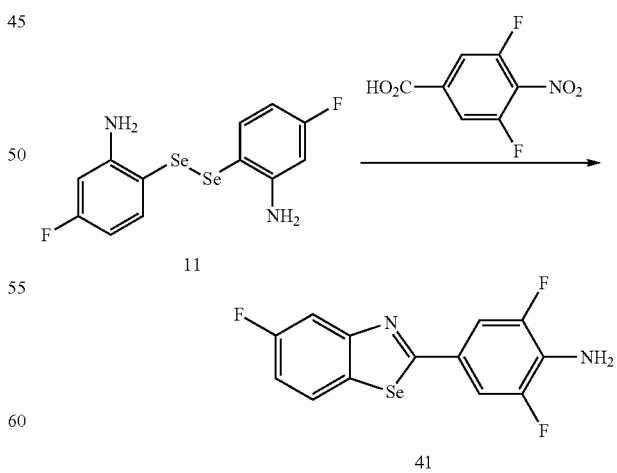

The method for preparing the compound 41 refers to the step A in Embodiment 13, wherein 3-fluoro-4-nitrobenzaldehyde in the step A of Embodiment 13 was replaced with 3,5-difluoro-4-nitrobenzaldehyde. $^1$H NMR (DMSO-d$_6$, 400

MHz) δ 8.18-8.14 (m, 1H), 7.79 (dd, J=2.4, 10.0 Hz, 1H), 7.62 (dd, J=2.4, 7.2 Hz, 2H), 7.26-7.21 (m, 1H), 6.11 (s, 2H). MS (El, m/z):327.0 [M−H]⁻.

Embodiment 18:

Synthesis of 2-fluoro-4-(5-fluorobenzoselenazole-2-yl)-6-methylaniline (45)

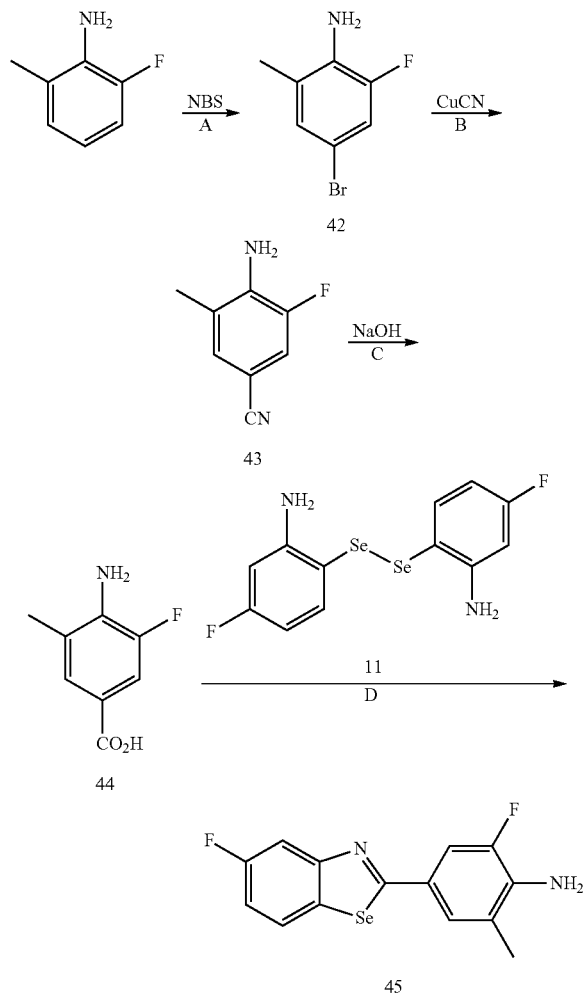

Step A: A solution of NBS (5.0 g, 28.1 mmol) in DMF (20 mL) was added dropwise into a solution of 2-fluoro-6-methylaniline (3.5 g, 28.0 mmol) in DMF (10 mL) in an ice-water bath, and the mixture was continuously stirred for 5 min at the end of addition. The ice-water bath was removed, and the reaction mixture was stirred 0.5 h at the room temperature. The mixture was added with water (150 mL) and extracted with ethyl acetate (80 mL×3), and the combined organic phase was successively washed with saturated sodium bicarbonate solution (40 mL×2) and saturated saline solution (40 mL×2), and dried with anhydrous sodium sulfate. The solvent was evaporated under reduced pressure to obtain 4-bromo-2-fluoro-methylaniline (42) (5.3 g). The yield was 92.8%.

Step B: A mixture of the compound 42 (5.3 g, 26.0 mmol), cuprous cyanide (3.0 g, 33.5 mmol) and N-methylpyrrolidone (15 mL) was stirred overnight under nitrogen at 180□. The mixture was added with water (75 mL) and extracted with ethyl acetate (50 mL×3), and the combined organic phase was successively washed with water (30 mL×2) and saturated saline solution (30 mL) and dried with anhydrous sodium sulfate. The solvent was evaporated under reduced pressure, and the product was purified by chromatography (200 to 300 meshes of silica gel, elution with ethyl acetate: petroleum ether=1:30 to 1:5) to obtain 4-amino-3-fluoro-5-methylbenzonitrile (43) (2.96 g). The yield was 75.8%.

Step C: A mixture of the compound 43 (2.95 g, 19.6 mmol), 1M sodium hydroxide solution (50 mL) and ethanol (5 mL) was refluxed and stirred overnight. The mixture was cooled to the room temperature, added with water (50 mL) and washed with MTBE (20 mL×2), and the water phase is used as the product. The water phase was adjusted with 2M hydrochloric acid until the pH value was 3 to 4, and the solid was separated out. The mixture was filtered, and the filter cake was dried to obtain 4-amino-3-fluoro-5-methylbenzoic acid (44) (2.90 g). The yield was 87.5%.

Step D: Tributylphosphine (2.15 g, 10.6 mmol) was added into a mixture of the compound 11 (1.74 g, 4.60 mmol), the compound 44 (600 mg, 3.55 mmol) and methylbenzene (25 mL), and the mixture was refluxed and stirred for 48 h under nitrogen. The mixture was cooled to the room temperature, added with water (40 mL) and adjusted with 2M sodium hydroxide solution until the pH value was 9 to 10. The mixture was extracted with ethyl acetate (40 mL×3), and the combined organic phase was washed with saturated saline solution (25 mL) and dried with anhydrous sodium sulfate. The solvent was evaporated under reduced pressure, and the product was purified by chromatography (200 to 300 meshes of silica gel, elution with ethyl acetate: petroleum ether=1:100 to 1:30) to obtain 2-fluoro-4-(5-fluorobenzoselenazole-2-yl)-6-methylaniline (45). ¹H NMR (DMSO-d₆, 400 MHz) δ 8.14-8.10 (m, 1H), 7.77-7.74 (m, 1H), 7.58-7.55 (m, 1H), 7.51 (s, 1H), 7.22-7.17 (m, 1H), 5.76 (s, 2H), 2.22 (s, 3H). MS (El, m/z):323.0 [M−H]⁻.

Bioactivity Embodiments

Embodiment 19: inhibition effects of the compounds on the growth of breast cancer cell Lines of MCF-7 and MDA-MB-468

Experimental Methods and Results

1. Breast cancer cells MCF-7 (Luminal type cells) and MDA-MB-468 (basal-like cells, which are of the triple-negative type without epithelial-mesenchymal transition) were purchased from Cell Resource Center of Shanghai Institutes for Biological Sciences of the Chinese Academy of Sciences, and cultured with DMEM culture medium(containing 10% of fetal bovine serum, 10 U/mL of penicillin and 0.1 mg/mL of streptomycin) in a 5% CO2 incubator at 37□ until the cell density was about 90%.

2. The cells were inoculated to a 96-well plate at a cell population of $3 \times 10^3$/well and then cultured in the 5% $CO_2$ incubator for 24 h at 37□.

3. Tested compounds of different concentration gradients were prepared by using the DMEM culture medium, and added into wells at 100 μL/well as tested compounds wells; and, the DMEM culture liquid was added into wells at 100 μL/well as negative control wells. At 37□ and in the 5% $CO_2$ incubator, the MCF-7 cells were cultured for 120 h, and MDA-MB-468 cells were cultured for 72 h.

4. Resazurin (15 mg/50 mL), Methylene Blue (25 mg/10 mL), Potassium ferricyanide (0.329 g/100 mL) and Potassium ferrocyanide (0.422 g/100 mL) were dissolved into PBS (0.1 M, pH=7.4) to obtain Alamar Blue solution for standby.

5. The cells were washed with PBS (0.1 M, pH=7.4) for two times, and the Alamar Blue solution was added into wells at 100 μL/well; and 100 μL of Alamar Blue solution was added into wells without cells to serve as blank control cells. The 96-well plate was placed into the 5% CO₂ incubator at 37□ and cultured for 3 h.

6. The fluorescence value of the cells was detected at 530/590 nm by ELIASA Victor X4 (Perkin Elmer). The fluorescence value at each concentration was repetitively measured for 4 times to obtain an average value and a standard deviation. The cell viability was calculated by the following formula[User2]:

$$\text{Cell viability (\%)} = \frac{\text{tested compound wells} - \text{blank control wells}}{\text{negative control wells} - \text{blank control wells}} \times 100\%$$

7. The half inhibitory concentration (IC$_{50}$) of the tested compounds againstt he cell lines was obtained according to the cell viability by Prism Graph software. The experimental results are shown in Table 1.

TABLE 1

Half inhibitory concentration (IC$_{50}$, nM) of the compounds againstcell lines ofMCF-7 and MDA-MB-468

| Compound ID | MCF-7 | MDA-MB-468 |
|---|---|---|
| 7 | 56.69 | 74.07 |
| 14 | 187.71 | 137.94 |
| 17 | 72.81 | 58.45 |
| 18 | 91.86 | 70.93 |
| 26 | 133.8 | |
| 34 | 52.38 | 29.06 |
| 35 | 41.59 | 39.67 |
| 37 | 449.56 | 113.63 |
| 41 | 56.77 | 20.1 |
| Paclitaxel | 4.6* | 4.43 |

*Note:
In Table 1, the positive control drugpaclitaxel has only 70% inhibition rate to MCF-7 cell line in itshighestconcentration at 500 nM. Therefore, the IC$_{50}$ of the paclitaxel for the MCF-7 cell strains calculated by the software is lower.

Embodiment 20: inhibition effects of the compounds on the growth of human lung cancer cells H1299, human colon cancer cells HT29, human liver cancer cells SK-HEP-1, human colon cancer cells HCT116, human normal liver cells L-02 and WRL-68

Growth inhibition tests of the tested compounds 7, 17, 18, 34, 35 and 41 on the human lung cancer cells H1299, human colon cancer cells HT29, human liver cancer cells SK-HEP-1, human colon cancer cells HCT116, human normal liver cells L-02 and WRL-68 were conducted, and the method refers to Embodiment 19 "Inhibition effects of the compounds on the growth of breast cancer cells MCF-7 and MDA-MB-468". The compounds 7, 17, 18, 34, 35 and 41 had a half inhibitory concentration (IC$_{50}$) greater than 10 μM for the cells, and had no obvious inhibition effects. The half inhibitory concentration (IC$_{50}$) of the positive control drug paclitaxel for the six cell lines was within a range of 1.59 nM to 15.31 nM.

The experimental results indicated that the compounds 7, 17, 18, 34, 35 and 41 had very good growth inhibition effects on the breast cancer cells MCF-7 and MDA-MB-468; and the half inhibitory concentration (IC$_{50}$) for other tested cell strains such as H1299, HT29, SK-HEP-1, HCT116, L-02 and WRL-68 was greater than 10 μM; and, the positive medicine paclitaxel still had strong inhibition toxicity on cancer cells in addition to the breast cancer cells and normal cells. Therefore, it was indicated that the compounds of the present application had remarkable selectivity for the inhibition of breast cancer cell lines.

What is claimed is:
1. A compound having general formula (II) shown as following, or its pharmaceutically acceptable salts thereof or prodrugs thereof:

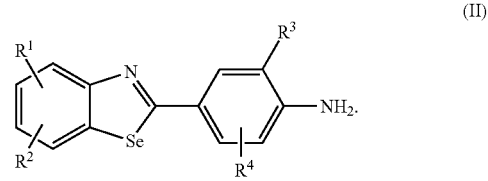

(II)

wherein:
R$^1$ and R$^2$ are independently selected from a group consisting of H, D, halogen, —CN, C$_{1-3}$ alkyl, substituted C$_{1-3}$ alkyl, C$_{1-3}$ alkoxy or substituted C$_{1-3}$ alkoxy, and the substituent group is selected from D, halogen and C$_{1-3}$ alkoxy;
R$^3$ is selected from a group consisting of halogen, —OH, —CN, —NH$_2$, substituted —NH$_2$, C$_{1-3}$ alkyl, substituted C$_{1-3}$ alkyl, C$_{1-3}$ alkoxy or substituted C$_{1-3}$ alkoxy, and the substituent group is selected from D, halogen, C$_{1-3}$ alkyl and C$_{1-3}$ alkoxy; and
R$^4$ is selected from a group consisting of H, D, halogen, —OH, —CN, —NH$_2$, substituted —NH$_2$, C$_{1-3}$ alkyl, substituted C$_{1-3}$ alkyl, C$_{1-3}$ alkoxy or substituted C$_{1-3}$ alkoxy, and the substituent group is selected from D, halogen, C$_{1-3}$ alkyl and C$_{1-3}$ alkoxy.

2. The compound according to claim 1, wherein:
R$^1$ and R$^2$ are independently selected from a group consisting of H, D, halogen, —CN, C$_{1-3}$ alkyl, substituted C$_{1-3}$ alkyl, C$_{1-3}$ alkoxy or substituted C$_{1-3}$ alkoxy, and the substituent group is selected from D, F and C$_{1-3}$ alkoxy;
R$^3$ is selected from a group consisting of halogen, —OH, —CN, —NH$_2$, substituted —NH$_2$, C$_{1-3}$ alkyl, substituted C$_{1-3}$ alkyl, C$_{1-3}$ alkoxy or substituted C$_{1-3}$ alkoxy, and the substituent group is selected from D, F, C$_{1-3}$ alkyl and C$_{1-3}$ alkoxy; and
R$^4$ is selected from a group consisting of H, D, halogen, —OH, —CN, —NH$_2$, substituted —NH$_2$, C$_{1-3}$ alkyl, substituted C$_{1-3}$ alkyl, C$_{1-3}$ alkoxy or substituted C$_{1-3}$ alkoxy, and the substituent group is selected from D, F, C$_{1-3}$ alkyl and C$_{1-3}$ alkoxy.

3. The compound according to claim 1, wherein R$^1$ and R$^2$ are independently selected from a group consisting of H, D, F, Cl, —CN, —CH$_3$, —CF$_3$, —OCH$_3$, —OCH$_2$CH$_3$, —OCF$_3$ and —OCHF$_2$.

4. The compound according to claim 1, wherein R$^3$ is selected from a group consisting of halogen, —OH, —CN, —NH$_2$, —CH$_3$, —CH$_2$CH$_3$, —CF$_3$, —OCH$_3$, —OCH$_2$CH$_3$, —OCHF$_2$ or —OCF$_3$, and R$^4$ is selected from H, D, halogen, —OH, —CN, —NH$_2$, —CH$_3$, —CH$_2$CH$_3$— CF$_3$, —OCH$_3$, —OCH$_2$CH$_3$,—OCHF$_2$ and —OCF$_3$.

5. The compound according to claim 1, wherein R$^1$ and R$^2$ are independently selected from a group consisting of H, D, F, Cl, —CN, —CH$_3$, —CF$_3$ or —CHF$_2$; R$^3$ is selected from F, Cl, Br, I, —CN, —CH$_3$, —CF$_3$, —OCH$_3$, —OCH$_2$CH$_3$, —OCHF$_2$ or —OCF$_3$; and, R$^4$ is selected from H, D, F, Cl, Br, I, —CN, —CH$_3$, —CF$_3$, —OCH$_3$, —OCH$_2$CH$_3$, —OCHF$_2$ and —OCF$_3$.

6. The compound according to claim 1, wherein the compounds are selected from a group consisting of 4-(benzoselenazole-2-yl)-2-bromoaniline,
2-bromo-4-(5-fluorobenzoselenazole-2-yl)aniline,
4-(5-fluorobenzoselenazole-2-yl)-2-methylaniline,
2-bromo-4-(5-fluorobenzoselenazole-2-yl)-6-methylaniline,
4-(5-bromobenzoselenazole-2-yl)-2-chloroaniline,
2-methyl-4-(5-methylbenzoselenazole-2-yl)aniline,
2-methyl-4[5-(trifluoromethyl)benzoselenazole-2-yl]aniline,
4-(6-ethoxybenzoselenazole-2-yl)-2-methylaniline,
4-(6-ethoxy-5-fluorobenzoselenazole-2-yl)-2-methylaniline,
2-fluoro-4-(5-fluorobenzoselenazole-2-yl)aniline,
2-bromo-6-fluoro-4-(5-fluorobenzoselenazole-2-yl)aniline,
5-(5-fluorobenzoselenazole-2-yl)-2-methylaniline,
4-(5-deuterobenzoselenazole-2-yl)-2-methylaniline,
2,6-difluoro-4-(5-fluorobenzoselenazole-2-yl)aniline, and
2-fluoro-4-(5-fluorobenzoselenazole-2-yl)-6-methylaniline.

7. A pharmaceutical composition comprising a therapeutically effective amount of the compound of claim 1, or its pharmaceutically acceptable salts thereof or prodrugs thereof, and pharmaceutically acceptable adjuvants.

8. A process for treating breast cancer comprising administering to a subject in need a therapeutically effective amount of the compound of claim 1, or its pharmaceutically acceptable salts thereof or prodrugs thereof.

* * * * *

UNITED STATES PATENT AND TRADEMARK OFFICE
CERTIFICATE OF CORRECTION

PATENT NO. : 10,005,744 B2
APPLICATION NO. : 15/572760
DATED : June 26, 2018
INVENTOR(S) : Dongfang Shi et al.

Page 1 of 1

It is certified that error appears in the above-identified patent and that said Letters Patent is hereby corrected as shown below:

On the Title Page

Item (72) should read:
(72) Inventors: Dongfang Shi, Fremont, CA (US); Changjin Fu, Jiangsu (CN); Xi Cheng, Jiangsu (CN); Jianghua Zhu, Jiangsu (CN)

Signed and Sealed this
Second Day of October, 2018

Andrei Iancu
*Director of the United States Patent and Trademark Office*